United States Patent [19]

Tucker, deceased

US005186935A

[11] Patent Number: 5,186,935

[45] Date of Patent: Feb. 16, 1993

[54] INSECTICIDAL BAIT COMPOSITION AND METHOD OF MAKING SAME

[75] Inventor: John W. Tucker, deceased, late of Boylston, Canada, by Dianne Tucker, executrix

[73] Assignee: Hedley Pacific Ventures, Ltd., Vancouver, Canada

[21] Appl. No.: 717,803

[22] Filed: Jun. 19, 1991

[30] Foreign Application Priority Data

Jun. 8, 1989 [CA] Canada .................................. 602158

[51] Int. Cl.$^5$ ...................... A01N 25/26; A01N 59/00
[52] U.S. Cl. .................................... 424/410; 424/405; 424/407; 424/724; 424/84; 514/949
[58] Field of Search ............... 424/405, 406, 407, 410, 424/84

[56] References Cited

U.S. PATENT DOCUMENTS

| | | | |
|---|---|---|---|
| 3,056,723 | 10/1962 | Galloway | 424/405 |
| 3,159,536 | 12/1964 | Marotta | 167/42 |
| 4,205,066 | 5/1980 | Hennart et al. | 424/84 |
| 4,279,895 | 7/1981 | Carle | 424/127 |
| 4,386,071 | 5/1983 | Carle | 424/127 |
| 4,849,216 | 7/1989 | Anderson | 424/84 |

FOREIGN PATENT DOCUMENTS

| | | | |
|---|---|---|---|
| 1112158 | 11/1981 | Canada | 167/3.7 |
| 1185172 | 4/1985 | Canada | 167/3.7 |
| WO85/04074 | 9/1985 | PCT Int'l Appl. | |

*Primary Examiner*—Thurman K. Page
*Assistant Examiner*—Neil S. Levy
*Attorney, Agent, or Firm*—Sixbey, Friedman, Leedom & Ferguson

[57] ABSTRACT

An insecticidal bait composition and method of making same, the composition comprising between about 92.5% to 98% by weight of a member selected from the group consisting of diatomaceous silica, crushed clamshells and mixtures thereof, the diatomaceous silica and/or clamshells being crushed to particles of a size of less than about 45 microns; between about 1.3% to 5% by weight honey; and between about 0.7% to 2.5% by weight paste yeast, the composition being prepared by agitating the ingredients of the composition together with water and drying the agitated ingredients to evaporate the water and crystallize the paste yeast and honey onto the particles. This composition is a safe insecticide, made from natural ingredients. It retains its potency well under external conditions including heat, cold and rain.

14 Claims, No Drawings

INSECTICIDAL BAIT COMPOSITION AND METHOD OF MAKING SAME

BACKGROUND OF THE INVENTION

Insecticidal compositions which are chemical in nature are well known. The chemicals upon which such compositions are based are capable of either instantaneously killing insects or paralyzing them. Such chemical compositions are increasingly causing concern to environmentalists for the pollution which they are causing to air, earth and water in regions where they are applied.

BACKGROUND OF THE INVENTION

Canadian Patent No. 1,185,172 of Carle issued Apr. 9, 1985, his earlier Canadian Patent No. 1,112,158 issued Nov. 10, 1981, as well as his U.S. Pat. Nos. 4,279,895 issued Jul. 21, 1981 and U.S. Pat. No. 4,386,071 issued May 31, 1983, describe natural bait insecticidal compositions which use, as their central ingredient, diatomaceous silica of a particle size at most 50 microns. Those patents have drawn on teachings, such as those contained in Marotta U.S. Pat. No. 3,159,536 issued Dec. 1, 1964, that insect pests may be killed by contacting them with dry, amorphous, particulate, hydrophilic siliceous materials such as diatomaceous earths. The thinking is that very small particles of diatomaceous silica and the like have very sharp edges which, when they come in contact with the exoskeleton of an insect, scratch through its protective waxy layer causing it to die from desiccation and dehydration. When such particles are ingested by an insect, the death of the insect is accelerated by internal desiccation. Such compositions however are neither toxic nor injurious to humans and warm blooded domestic animals.

The Canadian and U.S. patents to Carle, referred to previously herein, are directed towards compositions which use diatomaceous silica as their main ingredient, but which additionally incorporate compounds which tend to attract the insects. Thus, in Canadian Patent No. 1,185,172, diatomaceous silica is combined with water as well as yeast and/or skim milk. Yeast and skim milk have been ascertained to be attractants for insects. In Canadian Patent No. 1,112,158, diatomaceous silica which has been humidified is combined with sugar or a sugar substitute and water. The problem with such prior insecticidal bait compositions has been to prevent the attractant component from being washed away or otherwise separated from the diatomaceous earth component, for example by rain water or the like.

It is thus an object of the present invention to provide an insecticidal natural bait composition, based on diatomaceous silica, which will have improved retention of its insect-attractant qualities when exposed to external environmental conditions. It is a further object of the present invention to provide such a composition which is economical to produce and yet extremely lethal to a wide range of insects.

SUMMARY OF THE INVENTION

In accordance with the present invention there is provided an insecticidal bait composition comprising between about 92.5% to 98% by weight of a member selected from the group consisting of diatomaceous silica, crushed clamshells and mixtures thereof, the diatomaceous silica and/or clamshells being crushed to particles of a size of less than about 45 microns, between about 3% to 5% by weight honey and between about 0.7% to 2.5% by weight paste yeast. The composition is prepared by agitating the ingredients of the composition together with water and drying the agitated composition to evaporate the water and crystallize the paste yeast and honey onto the particles.

In a preferred embodiment, the honey and paste yeast are present in a relative ratio by weight of about 2:1.

The present invention also is directed to a method of making an insecticidal composition which comprises the steps of impregnating between about 85.5% to 96% by weight of a member selected from the group consisting of diatomaceous silica, crushed clamshells and mixtures thereof the diatomaceous silica and/or clamshells being crushed to particles of size of less than about 45 microns, with a hot liquid solution of between about 1.3% to 4.5% by weight honey, between about .7% to 2.5% by weight paste yeast and between about 2% to 7.5% by weight water, to produce a blend. The blend is then heated to evaporate water and crystallize the yeast and raw honey on the particles.

Again, it is preferred in such method that the honey and paste yeast are present in a relative ratio by weight of about 2:1.

The insecticidal bait composition prepared in accordance with the present invention results in the particles of diatomaceous silica or clamshells being coated with the attractant ingredients of the composition in a manner which even rain does not appear to wash off to any significant degree. The use of diatom shells as the silica ingredient provides an extremely cheap and available source for the main ingredient of this composition, thereby facilitating the economical production of such composition.

DETAILED DESCRIPTION OF THE INVENTION

Diatom shells have proven to be effective for use as the clamshells in the composition of this invention. Besides diatom shells (which contain as much as 35% calcium, but which are readily available and extremely cheap), other sources of silica may be used such as, for example, diatomaceous silica provided by Johns-Manville and marketed under the Trade Mark CELITE 209 and CELITE 322.

The preferred weight ranges of ingredients in preparing the insecticidal bait composition in accordance with the present invention are as follows:

(i) between about 85.5% to 96% by weight of the member selected from the group consisting of diatomaceous silica, crushed clamshells and mixtures thereof,
(ii) between about 1.3% to 4.5% by weight honey,
(iii) between about .7% to 2.5% by weight paste yeast, and
(iv) between about 2% to 7.5% by weight water.

The composition prepared in accordance with the present invention has considerable shelf-life. For instance, it has been stored in a non-heated shed during a Canadian winter, and has remained stable with little or no loss of potency. As well, the composition has been heated for 12 months at over 53° C. in a heat kiln and it has remained stable with little or no loss of potency.

The attractant paste yeast used in the composition of the present invention replicates the substance that insects themselves produce to attract other insects to food. The insects are attracted to the diatomaceous silica and/or clamshells by the paste yeast. As well, as a result of the honey used, an insect may also ingest the silica particles resulting in internal desiccation. It has been found that about a 2:1 ratio of honey to paste yeast is optimum for the composition in accordance with the present invention. As well, it has been found that too high a proportion of paste yeast results in too great attraction of insects so that, for example, in an urban environment, insects from neighboring yards would be attracted—a most undesirable result except for one's neighbors! The percentage range of paste yeast defined in the present invention results in attraction to insects over a range of about 5 to 10 meters from where the composition has been applied.

It has also been found that the greater the proportion of honey and paste yeast to silica, the longer the heating is required to produce crystallization after the blending.

The composition according to the present invention has the consistency and feel of a soft baby powder. It may be dusted around homes and gardens and produces, within 15 minutes to 48 hours, depending on the type of insect, its size and lifestyle, death for such insects. The following insects have been eliminated:

| cabbage looper | cockroaches | centipedes |
| millipedes | fleas | silverfish |
| carpet beetles | mites | bedbugs |
| cabbage worm | alfalfa caterpillar | budworm |
| celery looper | tomato hornworm | grape leaf folder |
| bag worm | spring cankerworm | fall cankerworm |
| elm spanworm | red humped caterpillar | tent caterpillar |
| earwigs | leafminers | sowbugs |
| caterpillars | leaf beetles | gypsy moth |
| aphids | leatherjackets | ants |
| webworm | slugs | |

The produce of the present invention is a safe insect eliminator and contains no chemicals or poisons. It is an odorless, non staining powder and can be used without fear of damage or harm to children, pets, food, fish, birds or wildlife.

For indoor use, the composition is lightly coated (dusted) in areas where insects are found or may hide such as in cracks and crevices, behind and under stoves, refrigerators, sinks, cabinets, garbage cans, around pipes and drains, window frames, in attics and basements. For fleas, sleeping areas of pets should be thoroughly dusted as well as surrounding cracks, crevices and baseboards. For carpet beetles, it should be dusted thoroughly beneath and along edges of carpets and rugs.

For outdoor use, the composition in powder form should be lightly dusted in areas where insects are found.

The following examples serve to further illustrate the invention.

EXAMPLE 1

To prepare an insecticidal bait composition in accordance with the present invention, the marine shells of clams known as diatoms are selected. The fresh water or salt water diatom is made up of minute marine planktonic uni-cells. These marine silicon dioxide shells are placed in a heat kiln at 53° C. for 72 hours to evaporate the moisture. The dried diatoms are then passed through a positive displacement pump which crushes them into a talcum-like powder and passed through a 325 mesh filter basket which results in no particle larger than about 44 microns.

Approximately 50 kg. of the powder is then placed into a barrel with dual agitators. A hot liquid solution consisting of 500 g. of paste yeast together with 1,000 g. of natural honey and 2.5 kg. of hot water is then placed into the barrel to impregnate the diatom particles. After about six hours in the barrel under agitation, the blend thus produced is inserted into a heat kiln at 43° C. for 6 hours to evaporate the moisture and crystallize the yeast and honey onto the diatom particles. The dried particles are then passed through the 325 mesh filter basket and are packaged for example in 200 g. hand spray bottles or in bulk packages of various sizes and weight.

EXAMPLE 2

The composition from Example 1 may be formulated into a wettable powder by mixing, for example, 1 kg. of powder to 10 liters of water. It can be applied by rotomist blower, hydraulic sprayer or hand back pack. The composition is exempt from residue tolerance so it can be sprayed on plants right up to harvest time.

The axial of the leaves act as holding cups for a composition in this liquid form. During the day the liquid evaporates and at night time the composition becomes mixed in liquid again.

EXAMPLE 3

200 g of the powder of Example 2 have been mixed with 10 liters of water and mixed well. The sod about the base of a Dutch elm tree has been turned back 250 mm, exposing the flare roots of the elm tree. 2.5 m. of the trunk, down to the flare root are then sprayed with the mixture, using up all 10 liters of the mixture per tree.

It has been found that the draft of the tree takes the mixture up through the complete tree and eliminates the elm beetle that is under the bark.

The composition of the present invention is effective in killing insects from the larva stage to that of full grown adult. Application of the composition enables the control of crop insects and household crawling insects, as well as, for example, preventing Dutch elm disease, willow blight and the like, without polluting or endangering the environment.

Thus it is apparent that there has been provided in accordance with the invention an insecticidal bait composition and method of making it that fully satisfies the objects, aims and advantages set forth above. While the invention has been described in conjunction with a specific embodiment thereof, it is evident that many alternatives, modifications and variations will be apparent to those skilled in the art in light of the foregoing description. Accordingly, it is intended to embrace all such alternatives, modifications and variations as fall within the spirit and broad scope of the invention.

What is claimed:
1. An insecticidal bait composition comprising:
    (a) between about 92.5% to 98% by weight of a member selected from the group consisting of diatomaceous silica, crushed clamshells and mixtures thereof, the diatomaceous silica and clamshells being crushed to particles of a size of less than about 45 microns;
    (b) between about 1.3% to 5% by weight honey; and
    (c) between about 0.7% to 2.5% by weight paste yeast, the honey and paste yeast being crystallized onto the particles by agitation with the particles together with water and baking the agitated ingredients to evaporate the water.

2. A composition according to claim 1, wherein the honey and paste yeast are present in a relative ratio by weight of about 2:1.

3. A composition according to claim 1, which has been passed through a filter basket of about 325 mesh after the paste yeast and honey have been crystallized under the particles.

4. A composition according to claim 1, comprising about 97% by weight crushed diatom shells, about 2% by weight honey and about 1% by weight paste yeast.

5. A composition according to claim 1, comprising about 97% by weight diatomaceous silica, about 2% by weight honey and about by weight paste yeast.

6. A composition according to claim 1, wherein the honey is raw honey.

7. A method of making an insecticidal composition which comprises the steps of:
   (i) impregnating between about 85.5% to 96% by weight of a member selected from the group consisting of diatomaceous silica, crushed clamshells and mixtures thereof, the diatomaceous silica and clamshells being crushed to particles of size of less than about 45 microns, with a hot liquid solution of between about 1.3% to 4.5% by weight honey, between about 0.7% to 2.5% by weight paste yeast and between about 2% to 7.5% by weight water to produce a blend, these ingredients to total 100% by weight; and
   (ii) heating the blend so as to crystallize the yeast and raw honey onto the particles.

8. A method according to claim 7, wherein the honey and paste yeast are present in a relative ratio by weight of about 2:1.

9. A method according to claim 7, utilizing the following ingredients in the following initial percentages by weight:
   (a) diatom shells about 92.6%
   (b) raw honey about 3.7%
   (c) paste yeast about 0.9%
   (d) water about 4.6%.

10. A method according to claim 8, wherein after heating of the blend so as to crystallize the yeast and honey on the particles, the composition is passed through a 325 mesh filter and collected for use as the insecticidal bait composition.

11. A method according to claim 7, wherein the particles are from crushed diatom shells.

12. A method according to claim 11, wherein diatom shells are heated to evaporate moisture and are then crushed and passed through a 325 mesh filter to produce a particle size of under about 45 microns, these crushed diatom shells then being impregnated with the honey, paste yeast and water solution.

13. A method according to claim 7, wherein the blend is heated at about 43° C.

14. An insecticidal bait powder comprising:
   (a) between 92.5% to 98% by weight of a particulate material of a particle size less than 45 microns selected from the group consisting of particulate diatomaceous silica, crushed clamshells and mixtures thereof; and
   (b) an insect attractant crystallized onto said particles to resist separation therefrom in response to moisture, said insect attractant being formed by a blend which includes
      (i) between 1.3% to 5% by weight honey; and
      (ii) between 0.7% to 2.5% by weight paste yeast with the relative ratio by weight of honey to paste yeast being 2:1, said honey and paste yeast having been heat crystallized onto the particles of particulate material.

* * * * *